US006783492B2

(12) United States Patent
Dominguez et al.

(10) Patent No.: US 6,783,492 B2
(45) Date of Patent: Aug. 31, 2004

(54) SYSTEM AND METHOD FOR MONITORING BODY FUNCTIONS

(76) Inventors: Steven Dominguez, 19 Bridington, Laguna Niguel, CA (US) 92677; Dennis J. Steibel, 1295 Thorndale La., Lake Zurich, IL (US) 60047; Richard D. Fraser, 2083 Westridge Blvd., Bartlett, IL (US) 60103

( * ) Notice: Subject to any disclaimer, the term of this patent is extended or adjusted under 35 U.S.C. 154(b) by 32 days.

(21) Appl. No.: 09/893,423

(22) Filed: Jun. 26, 2001

(65) Prior Publication Data

US 2002/0198445 A1 Dec. 26, 2002

(51) Int. Cl.[7] .................................................. A61B 5/00
(52) U.S. Cl. ...................... 600/365; 600/300; 128/920
(58) Field of Search .................. 600/365, 300, 600/301; 709/203; 705/3; 128/920, 923

(56) References Cited

U.S. PATENT DOCUMENTS

| 5,331,549 | A | * | 7/1994 | Crawford, Jr. ............... 128/700 |
| 5,544,661 | A | * | 8/1996 | Davis et al. ................. 128/700 |
| 5,997,476 | A | * | 12/1999 | Brown ........................ 600/301 |
| 6,053,887 | A | * | 4/2000 | Levitas et al. ................ 604/49 |
| 6,083,248 | A | * | 7/2000 | Thompson ................... 607/30 |
| 6,128,482 | A |   | 10/2000 | Nixon et al. |
| 6,171,237 | B1 |   | 1/2001 | Avitall et al. |
| 6,270,455 | B1 | * | 8/2001 | Brown ........................ 600/300 |
| 6,304,797 | B1 | * | 10/2001 | Shusterman ................ 700/243 |
| 6,350,237 | B1 | * | 2/2002 | Pelletier et al. .............. 600/300 |
| 6,368,273 | B1 | * | 4/2002 | Brown ........................ 600/300 |
| 6,383,136 | B1 | * | 5/2002 | Jordan ........................ 600/300 |
| 6,385,593 | B2 | * | 5/2002 | Linberg ....................... 705/28 |
| 6,459,933 | B1 | * | 10/2002 | Lurie et al. ..................... 607/5 |
| 2001/0044823 | A1 | * | 11/2001 | Labounty et al. ........... 709/203 |
| 2002/0013516 | A1 | * | 1/2002 | Freyre et al. ................ 600/300 |
| 2002/0045804 | A1 | * | 4/2002 | Christopherson et al. ... 600/300 |
| 2002/0077851 | A1 | * | 6/2002 | Cheng ........................... 705/2 |
| 2002/0077864 | A1 | * | 6/2002 | Cavallaro et al. .............. 705/3 |
| 2002/0120676 | A1 | * | 8/2002 | Biondi ........................ 709/223 |
| 2002/0128804 | A1 | * | 9/2002 | Geva .......................... 702/188 |
| 2002/0135336 | A1 | * | 9/2002 | Zhou et al. ................. 320/101 |

FOREIGN PATENT DOCUMENTS

| FR | 2717332 | * | 9/1995 |
| GB | 2285135 | * | 6/1995 |
| JP | 8-56910 | * | 3/1996 |
| JP | 2001-17398 | * | 1/2001 |
| WO | 01/97686 | * | 12/2001 |

* cited by examiner

*Primary Examiner*—John A. Jeffery

(57) ABSTRACT

A system for monitoring body functions from patients at remote locations that includes an event monitor attached to the patient including sensors attached to relevant parts of the patient for monitoring body functions. The system also includes a central monitoring station including a server having a memory attached thereto; and, a communication link between the event monitor and the central monitoring station. The method of this invention includes the steps of sensing the monitored body function by means of sensors attached to the patient. If any irregularities are detected, data indicative of the monitored body function is recorded and is automatically transmitted to the central monitoring station. The patient is located by means of GPS data; and a physician and the nearest hospital are notified. An attending physician may log onto the central monitoring station and observe real-time data received from the patient. Commands may be relayed to a medication dispensing device to aid in the immediate treatment of the patient.

20 Claims, 5 Drawing Sheets

SYSTEM AND METHOD FOR MONITORING BODY FUNCTIONS

BACKGROUND OF THE INVENTION

1. Field of the Invention

The present invention relates to a system and method for instantaneously monitoring body functions from patients at remote locations, automatically recognizing and causing the obtained abnormal data to be transmitted, allowing contemporaneous data and voice transmissions, and for locating a patient with a problem, which system also allows for a physician to receive data indicative or otherwise of the monitored body functions in real-time and in some instances to dispense medication to the patient from a remote location.

2. Description of Related Art

There have been numerous improvements in electronics useful in the monitoring of body functions, such as for example, heart arrhythmia, respiratory rate and solutes/glucose. Usually these devices will record data indicative of the body function, for example heartbeat or cardiovascular system or cardio-respiratory system, and store the data in a memory device. A patient wearing a 24-hour or a 30-day monitor will have data indicative of the monitored body function (e.g., heartbeat) recorded and stored in a memory device. The recorded data is then taken to a physician or technician for interpretation and comparison with reference data. In the example of a heart attack, the time lapse between the actual event that triggered the problem and the analysis of the recorded data may be too long to help the patient. This time lapse is typically 72 hours or more for a 24-hour monitor. It may be necessary to promptly dispense medicine or apply treatment to help overcome the problem detected and the time delay between the event and the analysis of the recorded data may prove to be too late. Moreover, it is necessary for the patient, or an attendant, to hook up the recording device to a telephone line and transmit the data to a receiving center.

In the above-described scenario, there is no true patient-health care professional interface. Hence, there is a problem where a heart patient has an arrhythmia or any form of cardiac dysfunction. The patient could fall and be injured, and no one would know about the problem or where the patient is located.

Therefore, a need exists for a system and method that will provide rapid or immediate access to data for analysis of a problem following the body function event being monitored, such as an irregular heartbeat, abnormal breathing pattern, or abnormal blood sugar. It is also desirable to be able to locate the patient in order to dispatch medical help or to immediately dispense medication.

SUMMARY OF THE INVENTION

Accordingly, it is an object of the present invention to provide a system that can monitor body function data and automatically relay this data to a central monitoring system in the event of a problem. Typically this could comprise cardiac monitoring, respiratory function monitoring, glucose monitoring, dialysis monitoring, etc.

Another object of the present invention is to provide a body function monitoring system that allows a physician, who may be situated at a completely different location than the patient being monitored, to observe data indicative of the monitored body function in substantially real-time.

Still another object of the present invention is to provide a system and method for monitoring body functions of a multiplicity of patients who are mobile and situated at a variety of different locations.

An advantage of the present invention is that patients may continue with a normal life style and have a vital body function, such as the heartbeat, monitored and made available in real time to medical technicians or physicians situated at completely different locations than the patient.

Another advantage of the present invention is that a physician may receive real-time data indicative of a monitored body function of their patients.

Still another advantage of the present invention is that the physician, who is at a remote location from the patient, can initiate the recording of more detailed data indicative of specifics of the monitored body function and receive a display in real-time of the data.

Yet another advantage of the present invention is that a patient can initiate the recording of data indicative of a monitored body function, whereupon the data is automatically transmitted to a central monitoring station for interpretation by medical personnel.

Another advantage of the invention is that the central monitoring station may remotely activate a medication dispensing device which is connected by way of cables, radio frequency, infrared or other means of communication, or is designed to be part of the event monitor, which receives commands from the central monitoring station to deliver medication to the patient. This medication dispensing device may be an Automatic Electronic Defibrillator, a diaphramitic or intercostal muscle stimulating device, an insulin or glucagon injector, or other device designed to immediately aid in the treatment of the patients body function abnormality. This device may also be connected to current intravenous pump machines, which deliver life saving medication to patients outside of the hospital setting, such as dobutamine or antibiotics.

These and other objects and advantages, which will become apparent as the invention is described in detail below, are provided by a system for monitoring body functions from patients at remote locations that includes an event monitor attached to the patient including sensors attached to relevant parts of the patient for monitoring body functions. The system also includes a central monitoring station including a server having a memory attached thereto; and, a communication link between the event monitor and the central monitoring station. The method of this invention includes the steps of sensing the monitored body function by means of sensors attached to the patient. If any irregularities are detected, data indicative of the monitored body function is recorded and is automatically transmitted to the central monitoring station. The patient may be located by means of GPS data, when available; and, a physician and the nearest hospital are notified. An attending physician may log onto the central monitoring station and observe real-time data received from the patient.

Still other objects, features and advantages of the present invention will become readily apparent to those skilled in the art from the following detailed description, wherein is shown and described only the preferred embodiment of the invention, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive, and what is intended to be protected by Letters Patent is set forth in the appended claims. The present invention will become apparent when taken in conjunction with the following description and attached drawings, wherein like characters indicate like parts, and which drawings form a part of this application.

BRIEF DESCRIPTION OF THE DRAWINGS

The general purpose of this invention, as well as a preferred mode of use, its objects and advantages will best be understood by reference to the following detailed description of an illustrative embodiment with reference to the accompanying drawings in which like reference numerals designate like parts throughout the figures thereof, and wherein.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically for a system and method that provides prompt feedback to medical technicians or physicians with detail data of a patient's monitored body function in the case of an aberrant event, such as a heart attack, slow or absence of breathing, high or low blood sugar level, etc.

Figure 1:
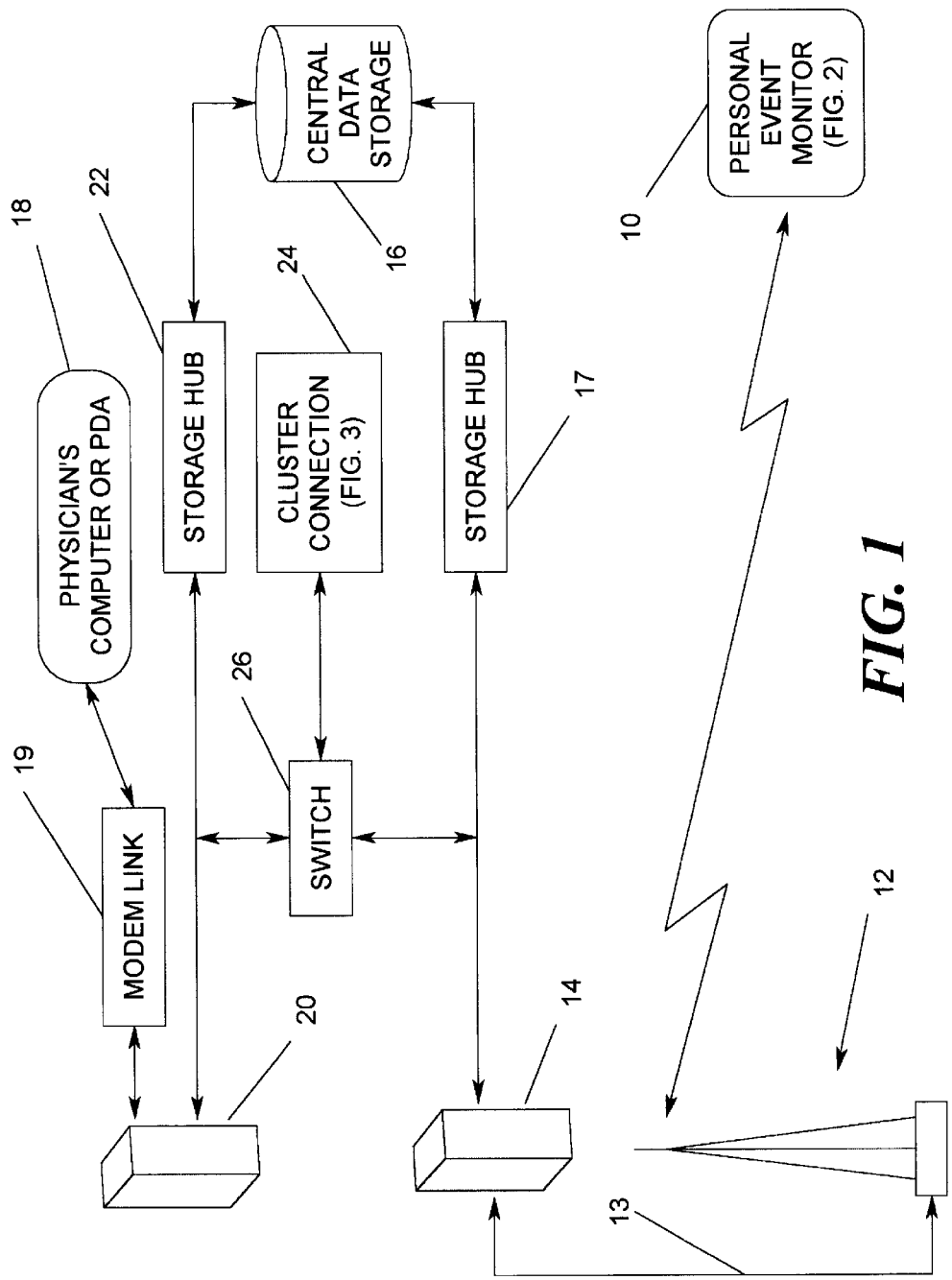
FIG. 1 is an overall block diagram of the system of the present invention.
Figure 2:
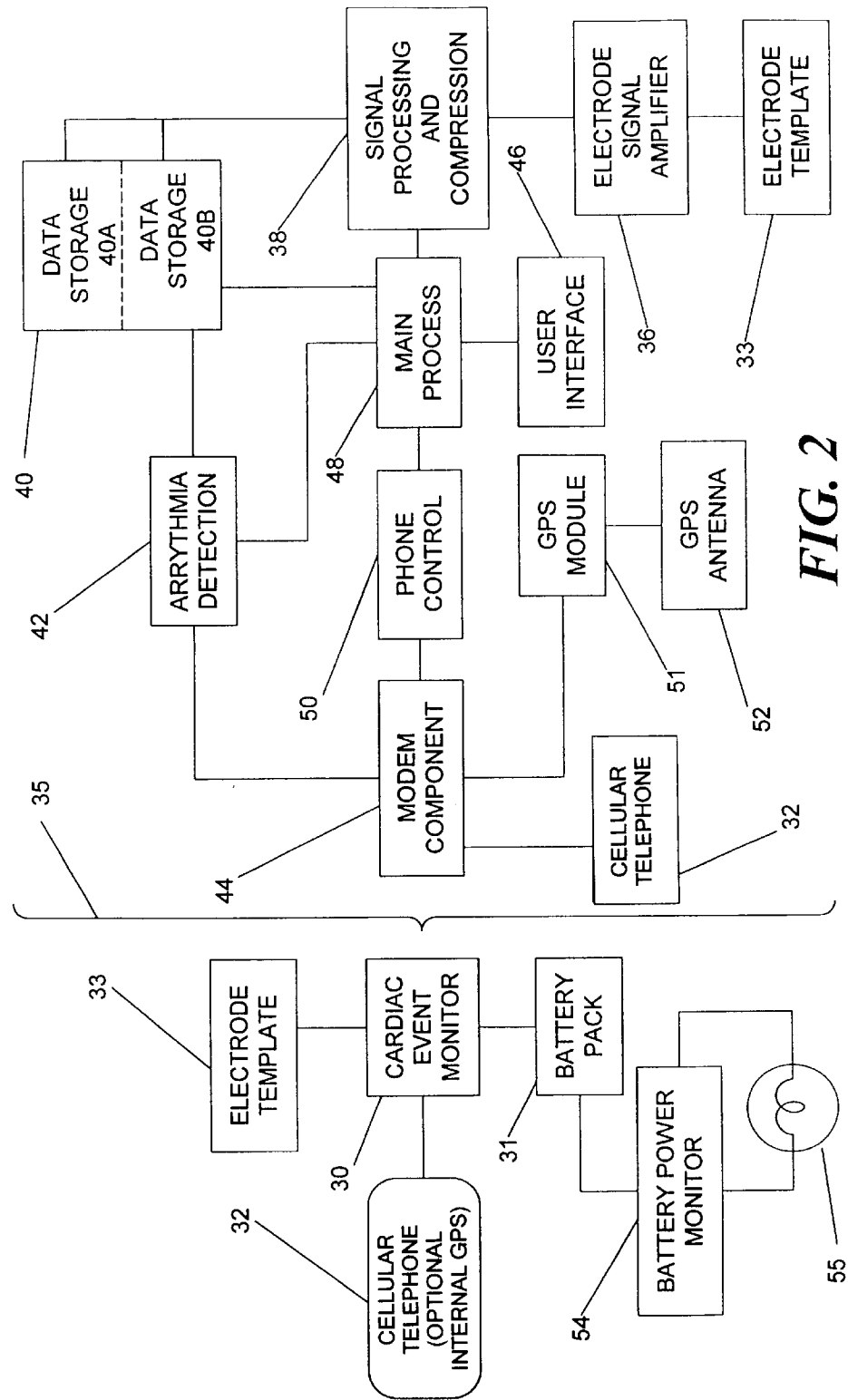
FIG. 2 is a block diagram of the personal body function monitor, which in one embodiment is a cardiac event monitor.

Referring now to the drawings and FIG. 1 in particular, a block diagram of the overall system of the present invention is shown. A personal event monitor 10, which is illustrated in FIG. 2 and amplified hereinbelow, is capable of transmitting data to a radio antenna 12. The antenna 12 relays this data, via telephone lines, a satellite link or a microwave link 13, to a server 14. The communication links between the personal event monitor 10 and the server 14 may comprise any of a variety of well-known techniques. The server 14 then stores the data in a central data storage 16 through a storage hub 17. A physician can access this data from a computer, such as a laptop computer or PDA 18, via a modem link 19 connected to a server 20. The server 20 can then access the same data as it arrives from the patient via the monitor 10 or patient data that was recorded earlier through a storage hub 22.

Figure 3:
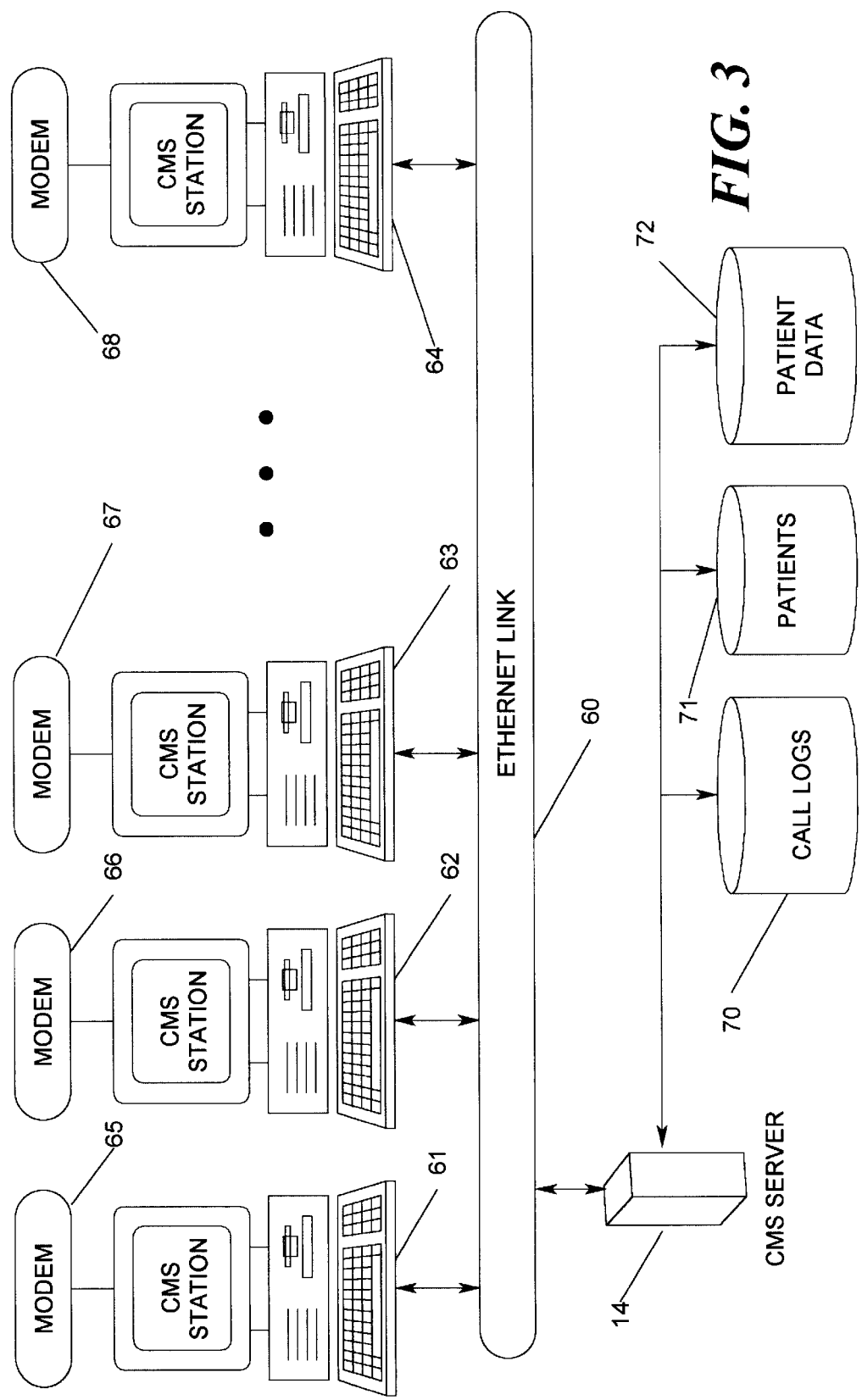
FIG. 3 is a block diagram of the central monitoring station ("CMS").

Alternatively, technicians who are located at a central monitoring station ("CMS") can access and monitor the data by means of a cluster connection 24, via a switch 26 that switches between the servers 14 and 20. The cluster connection comprises a bank of terminals or computers, which is illustrated in FIG. 3 and amplified hereinbelow. The server 14, storage hub 17 and central data may be located at the CMS or they may be located elsewhere and linked electronically to the CMS.

Referring now to FIG. 2, a block diagram of the personal event monitor 10 is shown. According to the illustrated embodiment, a cardiac event monitor 30 is at the center of the personal event monitor 10. A battery pack 31 provides power to the unit, and may typically comprise conventional batteries. A cellular telephone 32, with an optional internal GPS, is connected to the cardiac event monitor 30 for the purpose of transmitting data and for providing voice communication as well. A body function sensing device 33 is used for making physical contact with the patient and reading the body function to be monitored. An example of the body function sensing device 33 is the ECG Template disclosed in co-pending U.S. patent application Ser. No. 09/798,762, filed Mar. 2, 2001, and entitled DISPOSABLE ECG CHEST ELECTRODE TEMPLATE WITH BUILT-IN DEFIBRILLATION ELECTRODES by the same inventor hereof.

The output signals from the ECG electrode template 33 (worn by the patient) are provided as inputs to the electrode signal amplifier 36, whereupon these signals are processed and compressed by a signal processing and compression module 38. The processed and compressed signals are then stored in a data storage 40. These same signals are simultaneously applied to an arrythmia detection module 42 for detection of any irregularity of the detected heartbeats. It is pointed out that in accordance with one embodiment the data storage 40 comprises two separate memories 40A and 40B. Part 40A continuously stores heartbeats on a 24-hour basis. At the end of a 24-hour cycle, heartbeats are recorded over the previously recorded data. In other words, the part 40A records heartbeats in a continuous loop and is a volatile memory. Part 40B records heartbeats, which are recognized by the internal software as abnormal and or potentially life-threatening and thus meeting criteria for automatic transmission to the central monitoring station and is a volatile memory. The proprietary software may automatically initiate the contemporaneous recording and storage of the patient's 12-lead ECG into memory part 40B for transmission to the central monitoring station. In addition, the software and monitor may begin recording and storage of the patient's 12-lead ECG date upon receiving commands from the central monitoring station if it has not already done so.

If an irregularity is detected by the module 42, then a signal is passed to the main process 48, which then instructs the phone control 50 to establish a connection via a modem component 44 and the cellular telephone 32 with the central monitoring station (FIG. 3). The ECG data is then recorded on the volatile memory part 40B and is transmitted to the CMS server 14 at the same time. Moreover, the patient may initiate the monitoring process by means of a user interface 46 through a main process 48 and to both signal processing and compression module 38 and to a phone control 50. The patient's location is determined by means of a GPS antenna 52 linked to the global positioning satellite system, which location data is decoded by a GPS Module 51. The output of the module 51, i.e. location data, is coupled to the modem component 44 for transmission back to the CMS. A battery power monitor 54 is coupled to the battery pack 31 and to an indicator light 55, which illuminates when a test button (not shown) or a low-voltage state of the battery is sensed.

Referring now to FIG. 3, a block diagram of the CMS is shown. The server 14 is coupled to an Ethernet or equivalent link 60, which may be the same as the cluster connection 24 (FIG. 1). A multiplicity of terminals or CMS stations 61, 62, 63, and 64 (as shown) are coupled to the Ethernet link 60, and are disposed for use by medical personnel to observe the data received from the patients being monitored. The data is transmitted between the personal event monitor 10 and the central monitoring station server 14 over a cellular telephone network (i.e., via the cellular telephone 32, FIG. 2).

Each of the CMS stations are also coupled to modems 65, 66, 67 and 68 (as shown), respectively, for use with analog cellular phones.

The server 14 also has coupled thereto several databases containing data relative to the patients being monitored, which databases are stored within the central data storage 16 (FIG. 1). These databases may typically comprise call logs 70, a master list of patients 71 and individual data 72 for comparison with data received from a given patient.

Figure 4A:
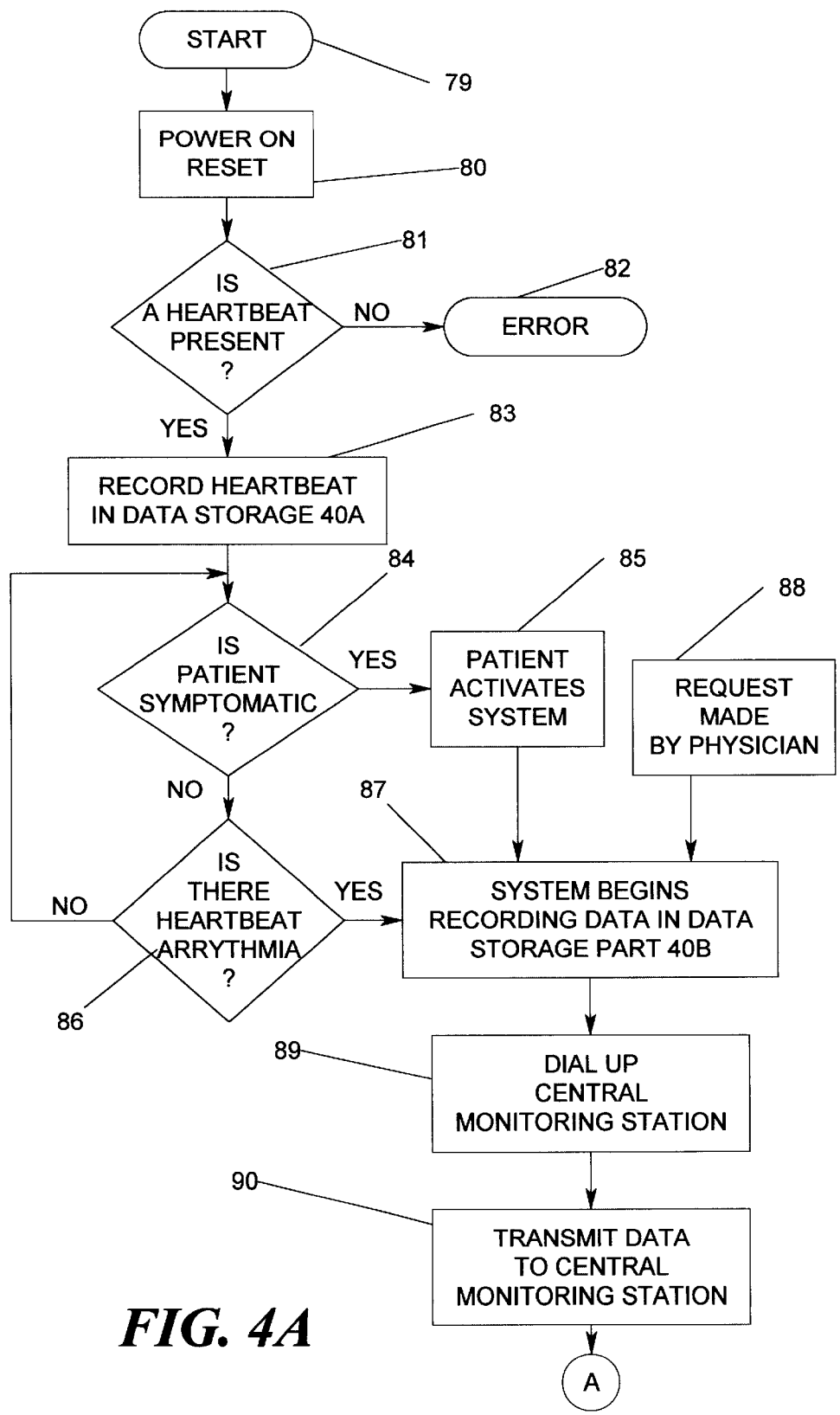
FIGS. 4A and 4B combined are a flow chart illustrating the method of the present invention.

Referring now to FIG. 4A, the process of the present invention occurring within the cardiac event monitor 30 is shown. The process begins with a start bubble 79 followed by a power on reset 80.

After this an inquiry is made as to whether or not a heartbeat is present (diamond 81). If the answer to this inquiry is no, then an error message is issued (bubble 82), which indicates that the electrode template on the patient may need adjustment of position or simply that the template is not present or connected. On the other hand, if a heartbeat is detected data indicative thereof is recorded into part 40A of the data storage 40 (block 83).

Following the above, another inquiry is made as to whether or not the patient is symptomatic (diamond 84). This condition occurs where the patient does not feel well and may be experiencing chest pains, palpitation, or dizziness. If the answer to this inquiry is yes, then the patient activates the system via the user interface 46 (FIG. 2) as denoted by a (block 85).

On the other hand, if the patient is not symptomatic, then yet another inquiry is made as to whether or not there is heartbeat arrythmia (diamond 86). If the answer to this inquiry is no, then a return is made back to the diamond 84. This loop will continue until a yes answer occurs in either the diamond 84 or 86. If the answer to the inquiry depicted by the diamond 86 is yes, then the system automatically begins recording data into part 40B of the data storage 40 (block 87). This data is also simultaneously transmitted to the CMS (FIG. 3). Moreover, if the patient activates the system (block 85) the system likewise begins recording data for transmission in the same manner as described above. Still another option is for the physician to make a request (block 88) to transmit patient data to the CMS.

Referring back to FIG. 2 momentarily, the physician's request to record (and transmit) patient data is made via the phone control 50 to the main process 48 to the signal processing and compression module 38, all as described hereinabove.

Now with reference back to FIG. 4A, once the system automatically begins recording patient data (block 87) the CMS is "dialed up" by the phone control 50 (block 89), and the modem component 44 is used for transmitting data to the CMS (Block 90). The process continues in FIG. 4B as denoted by a connector A. The patient monitor will automatically continue to dial up the central monitoring station and transmit data until it is commanded to cease transmission by the central monitoring station.

Figure 4B:
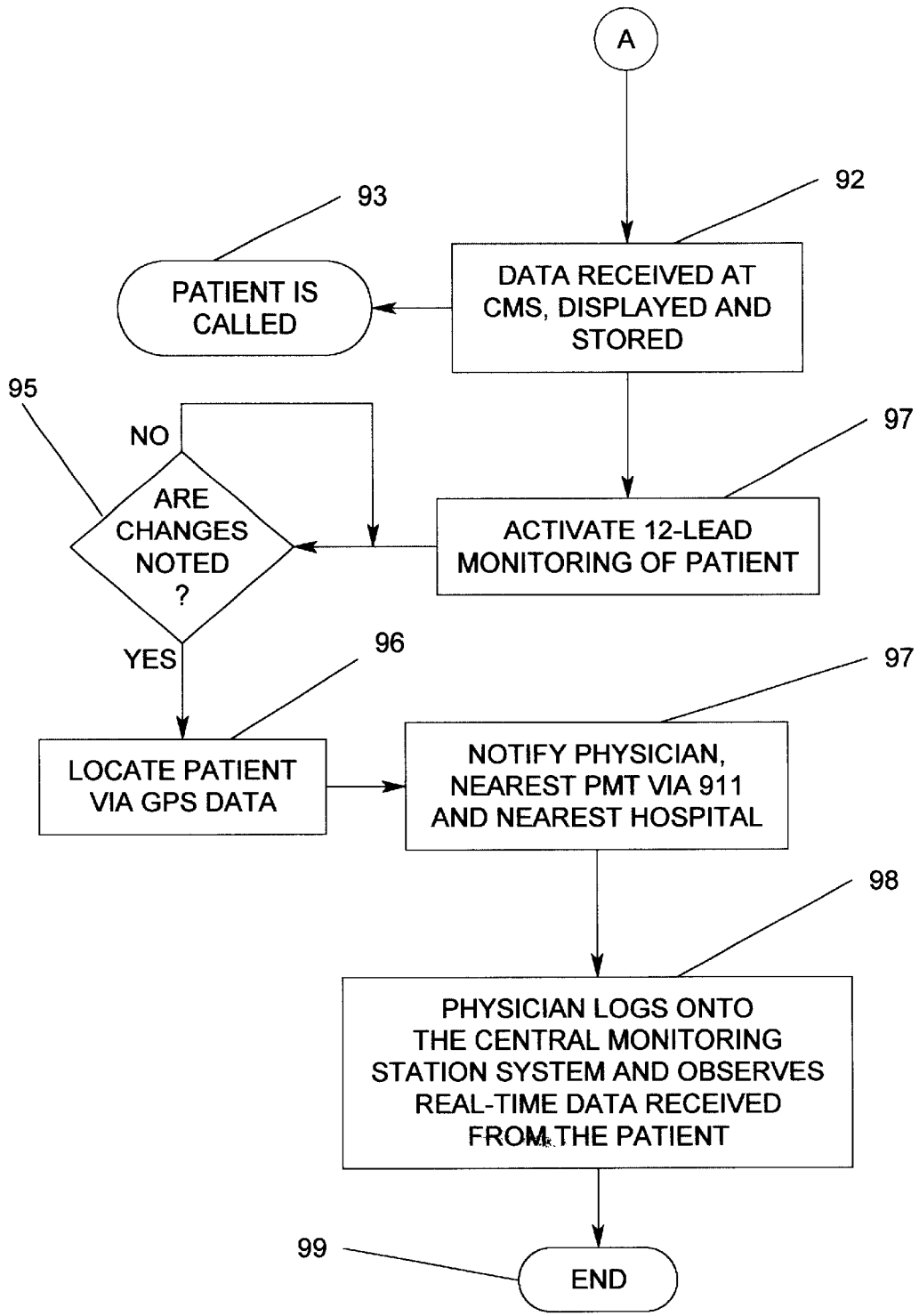

Referring now to FIG. 4B at the connector A, the relevant portion of the process occurring within the CMS is shown. First, the data received at the CMS is displayed on the CMS stations 61–64 (FIG. 3) and stored in the central data storage 16 (FIG. 1) (block 92). As soon as patient data is first received at the CMS, the patient is called (bubble 93). The patient is asked a series of questions regarding his condition or what activity was he just performing, which may have triggered the event.

After this, a 12-lead monitoring of the patient is activated (block 94). As explained above, the electrode template was initially recording data from only three leads. Now that a cardiac event, or the patient or the physician has activated the system, a full 12-lead monitoring of the patient is activated for increasing the data to be monitored and recorded.

As inquiry (diamond 95) is next made as to whether or not changes are noted after the patient's data has been compared with reference waveforms stored in the database 72. If the answer is no, then the inquiry is repeated until a change is noted. At this point the patient's location is determined either via phone contact or via GPS data (block 96). The physician is then notified as well as activation of the 911 pre-hospital care system, as well as the nearest hospital (block 97).

Once the physician has been notified, then he or she may log onto the CMS system and observe real-time data being received from the patient (block 98).

Further embodiments include a medication dispensing device which is connected by way of cables, radio frequency, infrared or other means of communication, or is designed to be part of the event monitor, which receives commands from the central monitoring station to deliver medication to the patient. This medication dispensing device may be an Automatic Electronic Defibrillator, a diaphramitic or intercostal stimulating device, an insulin or glucagon injector, or other device designed to immediately aid in the treatment of the patients body function abnormality. This device may also be connected to intravenous pump machines, which deliver life saving medication to patients outside of the hospital setting, such as dobutamine or antibiotics.

It is noted that the above system is applicable and designed to conform to all body functions monitored by sensing devices and is not limited in scope to the cardiac monitor described above and is intended for use with other body functions monitors such as respiratory, glucose and solute sensing devices, etc.

While the invention has been particularly shown and described with reference to a preferred embodiment, it will be understood by those skilled in the art that various changes in form and detail may be made therein without departing from the spirit and scope of the invention. The methods, techniques, technology, design of the invention is intended to apply to all body function monitoring as described hereinabove, wherever and whenever remote monitoring, data storage, data retrieval via delay or real time is conducted.

The methods and apparatus of the present invention, or certain aspects or portions thereof, may take the form of program code (i.e., instructions) embodied in tangible media, such as floppy diskettes, CD-ROMS, hard drives, or any other machine-readable storage medium, wherein, when the program code is loaded into and executed by a machine, such as a computer, the machine becomes an apparatus for practicing the invention. The methods and apparatus of the present invention may also be embodied in the form of program code that is transmitted over some transmission medium, such as over electrical wiring or cabling, through fiber optics, satellite links, or via any other form of transmission, wherein, when the program code is received and loaded into and executed by a machine, such as a computer, the machine becomes an apparatus for practicing the invention. When implemented on a general-purpose processor, the program code combines with the processor to provide a unique apparatus that operates analogously to specific logic circuits.

Those skilled in the art will appreciate that various adaptations and modifications of the just-described preferred embodiments can be configured without departing from the scope and spirit of the invention. Therefore, it is to be understood that within the scope of the appended claims, the invention may be practiced other than as specifically described herein.

What is claimed is:

1. A system for monitoring body functions of patients at remote locations, said system comprising:

a mobile event monitor to be attached to a patient, the mobile including reconfigurable sensors attached to relevant parts of said patient for monitoring body functions;

a central monitoring station including a server having a memory attached thereto;

a communication link between said event monitor and said central monitoring station, the communication link to permit the event monitor to send patient information to the central monitoring station and permit the central monitoring station to remotely reconfigure the sensors; and an automatic treatment device coupled to said patient, the automatic treatment device for providing direct medical treatment to the patient when instructed to do so.

2. The system according to claim 1 wherein said monitor is a cardiac event monitor sensing the heartbeat of said patient.

3. The system according to claim 1 wherein said communication link is a cell phone.

4. The system according to claim 1 wherein said communication link includes means for providing location data of said patient using GPS.

5. The system according to claim 1 wherein said event monitor includes a memory for storing relevant data about said patient.

6. The system according to claim 1 wherein said event monitor records the heartbeat of said patient.

7. The system according to claim 1 wherein said event monitor detects heartbeat arrythmia of said patient, further including means for automatically transmitting the patient heartbeat to said central monitoring station for recording and observation by medical personnel.

8. The system according to claim 7 wherein an operator can remotely reconfigure said sensor on said patient to record more detailed information about said heartbeat arrythmia.

9. The system according to claim 1 wherein said central monitoring station includes means for a physician at a remote location to access said monitored body function of said patient.

10. The system according to claim 1 wherein said central monitoring station selectively commands said automatic treatment device to deliver medical treatment to the patient when an irregular physical condition is sensed.

11. The system according to claim 1 wherein said event monitor senses respiratory functions of said patient.

12. The system according to claim 1 wherein said event monitor senses glucose levels of said patient.

13. The system according to claim 1 wherein said event monitor senses dialysis levels of said patient.

14. The system of claim 1 wherein the event monitor stores information related to the monitored body functions, the central monitoring station receives the information related to the monitored body functions obtained by the event monitor, and an operator can instruct event monitor to collect additional information about the patient's physical condition.

15. The system of claim 14 wherein the operator can instruct the automatic treatment device to deliver medical treatment to the patient when an irregular physical condition is sensed.

16. The system of claim 1 wherein the automatic treatment device is a device for immediately aiding in the treatment of a patient's body function abnormality.

17. The system of claim 1 wherein the automatic treatment device is an automatic electronic defibrillator.

18. The system of claim 1 wherein the automatic treatment device is either a diaphramitic or intercostal stimulating device.

19. The system of claim 1 wherein the automatic treatment device is either an insulin or glucagon injector.

20. A system comprising:

an event monitor including one or more reconfigurable sensors for monitoring one or more body functions of a person, a first data storage device to store information detected by the one or more sensors, wherein the event monitor compares the information detected by the one or more sensors to a reference data set and transmit the information if it indicates an irregular medical condition;

a central monitoring station communicatively coupled to the event monitor, the central monitoring station including a second data storage device to store sensor information received from the event monitor, wherein the central monitoring station receives the information transmitted by the event monitor and alerts an operator;

wherein the central monitoring station can remotely reconfigure the event monitor sensors; and an automatic treatment device communicatively coupled to the central monitoring station for immediately aiding in the treatment of a patient's body function abnormality, the automatic treatment device configured to provide direct medical treatment to a patient when instructed to do so by the operator at the central monitoring station.

* * * * *